United States Patent
Douezan et al.

(10) Patent No.: US 11,547,648 B2
(45) Date of Patent: Jan. 10, 2023

(54) COMPOSITION COMPRISING BAICALIN AND A PARTICULAR ACRYLIC POLYMER

(71) Applicant: L'OREAL, Paris (FR)

(72) Inventors: Stéphane Douezan, Chevilly la Rue (FR); Angélina Roudot, Chevilly la Rue (FR); Maud Willien, Chevilly la Rue (FR)

(73) Assignee: L'OREAL, Paris (FR)

( * ) Notice: Subject to any disclaimer, the term of this patent is extended or adjusted under 35 U.S.C. 154(b) by 207 days.

(21) Appl. No.: 16/759,622

(22) PCT Filed: Nov. 15, 2018

(86) PCT No.: PCT/EP2018/081472
§ 371 (c)(1),
(2) Date: Apr. 27, 2020

(87) PCT Pub. No.: WO2019/096957
PCT Pub. Date: May 23, 2019

(65) Prior Publication Data
US 2020/0297612 A1    Sep. 24, 2020

(30) Foreign Application Priority Data

Nov. 15, 2017 (FR) .................................... 1760728

(51) Int. Cl.
| | | |
|---|---|---|
| *A61K 8/60* | (2006.01) | |
| *A61K 8/06* | (2006.01) | |
| *A61K 8/81* | (2006.01) | |
| *A61Q 17/04* | (2006.01) | |

(52) U.S. Cl.
CPC ............... *A61K 8/602* (2013.01); *A61K 8/06* (2013.01); *A61K 8/8152* (2013.01); *A61Q 17/04* (2013.01)

(58) Field of Classification Search
None
See application file for complete search history.

(56) References Cited

U.S. PATENT DOCUMENTS

| 4,128,635 A | * | 12/1978 | Hase | .................... | A61K 8/8158 |
| | | | | | 514/772.4 |
| 2010/0233301 A1 | * | 9/2010 | Cheng | .................. | A61K 36/068 |
| | | | | | 424/773 |
| 2014/0107046 A1 | * | 4/2014 | Pan | ........................ | A61K 8/498 |
| | | | | | 514/456 |

OTHER PUBLICATIONS

"Regenerating Serum", Oct. 1, 2014, XP002780185.
"Mat Multi Benefit Integral Care For Combination to Oily Skin", Nov. 1, 2016 XP002780186.
Mintel "CC Cream Broad Spectrum SPF 30 PA+++", Sep. 1, 2014, XP002780187.
English Abstract of CN 104 382 793 A, Nov. 27, 2014, XP002780188.
English Abstract of CN 105 997 649 A, Jun. 17, 2016, XP002780189.

* cited by examiner

*Primary Examiner* — Nannette Holloman
(74) *Attorney, Agent, or Firm* — Polsinelli PC

(57) ABSTRACT

The present application relates to a composition for topical application comprising baicalin and/or at least one derivative thereof or an extract containing same, and at least one acrylic polymer, and to the use of said composition in the cosmetics and dermatology fields and in particular for caring for, for the hygiene of, for protecting and/or for making up bodily or facial skin, or for hair care, preferably for caring for bodily or facial skin. A subject of the invention is also a process for the cosmetic treatment of keratin materials, which consists in applying to the keratin materials a composition as defined above, and also the use of said composition in the cosmetics or dermatology field, and in particular for caring for, protecting and/or making up bodily or facial skin, or for hair care, preferably for caring for bodily or facial skin.

17 Claims, No Drawings

COMPOSITION COMPRISING BAICALIN AND A PARTICULAR ACRYLIC POLYMER

CROSS REFERENCE TO RELATED APPLICATIONS

This application is a National Phase filing under 35 U.S.C. § 371 of PCT/EP2018/081472 filed on 15 Nov. 2018; which application in turn claims priority to Application No. 1760728 filed in France on 15 Nov. 2017. The entire contents of each application are hereby incorporated by reference.

The present application relates to a composition, in particular for topical application, comprising baicalin and/or a derivative thereof or an extract comprising same, and at least one acrylic polymer, and to the use of said composition in the in particular non-therapeutic cosmetics and dermatology fields and in particular for caring for, for the hygiene of, for protecting and/or for making up keratin materials such as the skin, in particular bodily or facial skin, or the hair, preferably for caring for bodily or facial skin.

The present invention also relates to a composition, in particular for topical application, comprising baicalin and/or a derivative thereof or an extract containing same, at least one acrylic polymer and at least one UV-screening agent, and to the use of said composition in the in particular non-therapeutic cosmetics and dermatology fields and in particular for protecting keratin materials, in particular the skin and/or the lips and/or the hair, against solar radiation.

Many cosmetic compositions comprising baicalin, in particular as an antioxidant or as a photoprotective agent, or an extract containing same, are known in the prior art. Patent application EP 2 729 117 A1 in particular describes photoprotective compositions comprising baicalin.

The baicalin of formula (II) below:

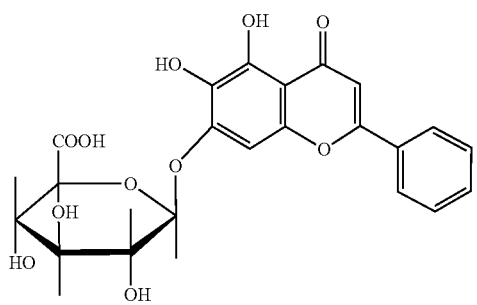

is a particularly beneficial polyphenol in cosmetics due to its antioxidant activity which makes it possible to treat or prevent the premature ageing of keratin materials such as the skin, induced by UV radiation or atmospheric agents such as pollutants.

However, the solubility of baicalin is very low in an aqueous medium, in particular at low pH values. Furthermore, at a pH above 6, baicalin is chemically unstable and liable to degrade.

Furthermore, one of the drawbacks lies in the fact that baicalin causes yellowing of the compositions comprising it, which is difficult to accept from a cosmetic point of view.

One technical problem therefore lies in the obtaining of a cosmetic composition comprising baicalin, or an extract containing same, which is stable and acceptable from a cosmetic point of view, and in particular which minimizes yellowing as much as possible.

In addition, in the photoprotection field, there is a constant need for compositions which make it possible to obtain a matte effect on the skin. Indeed, the shininess of the skin, which is generally linked to a high level of sebum secretion, is a problem which essentially affects adolescents but which may also occur in adults, especially as a consequence of hyperproduction of androgens or as a consequence of external factors such as pollution. The shininess of the skin may also be linked to sweat resulting from physical activity or climatic conditions (heat, humidity). The shininess of the skin may be due to the combination of these two phenomena (sebum and sweat).

Obtaining a matte effect on the skin is highly desired by users who have combination skin or oily skin, and also for cosmetic compositions that are intended to be used in hot and humid climates. Indeed, the reflections caused by an excess of sebum and/or sweat on the surface of the skin are generally considered to be unattractive. Shiny skin also generally gives rise to poorer staying power of the makeup, which thus has a tendency to become degraded over the course of the day.

Another technical problem thus lies in the obtaining of a cosmetic composition comprising baicalin, which makes it possible to obtain a matte effect on the skin.

Finally, there is a need for cosmetic compositions, in particular care or makeup compositions, comprising baicalin, or an extract containing same, which are fresh on application and non-greasy.

The inventors have now demonstrated that the combination of baicalin and/or a derivative thereof or an extract containing same and of at least one polymer b) described below makes it possible to minimize the yellowing of baicalin in compositions which contain it.

In addition, such compositions have good properties for mattifying oily and/or shiny skin. They are also fresh and non-greasy on application.

Thus, a subject of the present invention is a composition for topical application comprising baicalin and/or at least one derivative thereof or an extract containing baicalin and/or at least one derivative thereof, and at least one polymer b) described below.

Moreover, the addition of the polymer b) described below to the composition comprising baicalin and/or a derivative thereof or an extract comprising same makes it possible to satisfactorily thicken it, the thickening properties of the polymer not being impaired during the pH variations required for dissolving the baicalin and/or derivatives thereof.

Furthermore, the texture of the composition thus obtained is very satisfactory, in particular in terms of consistency, as are its sensory properties, with in particular a fresh, soft, non-greasy and non-tacky feeling on the skin, during and after application. The composition according to the invention is stable over time and/or when it is subjected to temperature variations.

Moreover, the composition according to the invention is easy to spread on the skin, and the film obtained on the skin is uniform. This property is all the more pleasing when the composition is used for anti-sun protection.

Thus, a subject of the present invention is also a composition, and in particular a cosmetic composition, comprising baicalin and/or at least one derivative thereof or an extract containing baicalin and/or at least one derivative thereof, at least one polymer b) described below and at least one UV-screening agent.

According to one particular embodiment, the composition in accordance with the invention comprises baicalin or an extract containing same, at least one polymer b) described below and at least one UV-screening agent.

A subject of the invention is also a process for the cosmetic treatment of keratin materials, which consists in applying to the keratin materials one of the two compositions as defined above.

A subject of the invention is also the use of one of the two compositions in the in particular non-therapeutic cosmetics or dermatology field, and in particular for caring for, protecting and/or making up bodily or facial skin, or for hair care, preferably for caring for and/or protecting bodily or facial skin.

The present invention also relates to the use, in particular cosmetic use, of a composition according to the invention, for reducing UV-induced pigmentation.

The present invention also relates to a cosmetic process for caring for and/or making up the skin and/or the lips and/or the hair, comprising the topical application to the skin and/or the lips and/or the hair of the composition according to the invention.

The present invention also relates to a cosmetic and/or aesthetic care method comprising the topical application to the skin and/or the lips and/or the hair of a composition according to the invention for combating or preventing photo-induced premature ageing of the skin and/or of the lips and/or of the hair.

The present invention also relates to a cosmetic and/or aesthetic care method comprising the topical application to the skin and/or the lips of a composition according to the invention for protecting the skin and/or the lips and/or the hair against solar radiation.

Finally, the present invention also relates to the use of the polymer b) according to the invention for reducing the yellowing of a composition comprising at least baicalin and/or a derivative thereof or a plant extract comprising it.

A composition in accordance with the invention, namely intended for the implementation of the invention, may be a non-therapeutic cosmetic or dermatological composition according to the application envisaged, and therefore comprises a physiologically acceptable medium.

For the purposes of the present invention, a physiologically acceptable medium can be a dermatologically or cosmetically acceptable medium, preferably a cosmetically acceptable medium, i.e. devoid of any unpleasant appearance or odour, and which is entirely compatible with topical administration to the skin and the skin appendages, and compatible with all keratin materials.

In the context of the present invention, the term "keratin material" is in particular intended to mean the skin, the scalp, keratin fibres such as the eyelashes, the eyebrows, head hair, bodily hair, the nails, and mucous membranes such as the lips, and more particularly the skin (body, face, area around the eyes, eyelids).

In the present case, the composition is intended to be administered topically, i.e. by application at the surface of the keratin material under consideration, and more particularly of the skin under consideration.

The cosmetic or dermatological compositions capable of being used in the context of the invention generally comprise a physiologically acceptable medium, preferably a cosmetically acceptable medium.

In the following text, the expression "at least one" is equivalent to "one or more", and, unless otherwise indicated, the limits of a range of values are included in that range.

Baicalin and Derivatives or Extracts Comprising Same

The compositions according to the invention comprise baicalin and/or at least one derivative thereof or a plant extract containing baicalin and/or at least one derivative thereof.

Baicalin and derivatives thereof have been described, as have the processes for the preparation thereof, in particular in application WO 2005/044281. They are chosen from the compounds of formula (I) below:

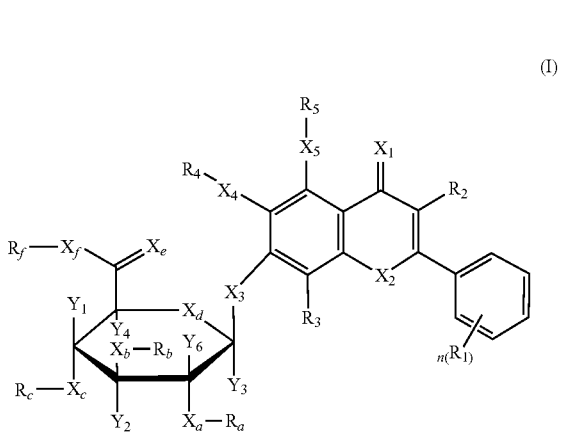

(I)

in which:

each $X_1$, $X_2$, $X_3$, $X_4$, $X_5$, $X_a$, $X_b$, $X_c$, $X_d$, $X_e$ and $X_f$ independently denotes O or S;

each $Y_1$, $Y_2$, $Y_3$, $Y_4$, $Y_5$, $Y_6$ independently denotes H or a $(C_1-C_{10})$alkyl radical, in particular a methyl radical;

each $R_4$, $R_5$, $R_a$, $R_b$ and $R_c$, independently denotes H, a $(C_1-C_{10})$alkyl radical optionally substituted with 1 to 5 groups $R_y$, or a $(C_1-C_{10})$alkyl-O—$(C_1-C_{10})$alkyl radical, each $(C_1-C_{10})$alkyl radical possibly being substituted with 1 to 5 groups $R_y$; each $R_y$, independently denotes $R_q$ or a —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$tricycloalkenyl, phenyl, naphthyl, —$(C_{14})$aryl radical, each possibly being substituted with one or more radicals $R_z$; each $R_1$, $R_2$, $R_3$, independently denotes $R_q$ or a —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$tricycloalkenyl, phenyl, naphthyl, —$(C_{14})$aryl radical, each possibly being substituted with one or more radicals $R_z$;

Rf is H, $(C_1-C_{12})$ alkyl optionally substituted with 1 to 5 radicals $R_y$, $(C_1-C_{12})$alkyl-O—$(C_1-C_{12})$alkyl, each $(C_1-C_{12})$ alkyl radical possibly being substituted with 1 to 5 groups $R_y$;

each $R_q$, independently is CN, OH, halogen, $N_3$, $NO_2$, $N(R_z)_2$, =$NR_z$, CH=$NR_z$, $NR_zOH$, $OR_z$, $COR_z$, $C(O)R_z$, $O(CO)OR_z$, $SR_z$, $S(O)R_z$ or $S(O)_2R_z$;

each $R_z$, independently is —$(C_1-C_6)$alkyl, —$(C_2-C_6)$alkenyl, —$(C_3-C_8)$cycloalkyl, —$(C_3-C_8)$cycloalkenyl, phenyl, a heterocycle having 3 to 5 branches, CH(halo)$_2$ or C(halo)$_3$; and n is 0, 1, 2, 3, 4 or 5;

and also the salts thereof, the optical isomers thereof and the diastereoisomers thereof.

Some compounds of formula (I) may have asymmetric centres and exist in different enantiomeric and diastereoisomeric forms. A compound of formula (I) may be in the form of an optical isomer or a diastereoisomer. According to the invention, the compounds of formula (I) also comprise their optical isomeric or diastereoisomeric forms and mixtures thereof, including racemic mixtures.

The term "—($C_1$-$C_{10}$)alkyl" is intended to mean a saturated, linear or branched non-cyclic hydrocarbon-based chain having from 1 to 10 carbon atoms. As examples of saturated linear —($C_1$-$C_{10}$)alkyl radicals, mention may be made of: methyl, ethyl, n-propyl, n-butyl, n-pentyl, n-hexyl, n-heptyl, n-octyl, n-nonyl and n-decyl. As examples of saturated branched —($C_1$-$C_{10}$)alkyl radicals, mention may be made of isopropyl, sec-butyl, isobutyl, tert-butyl, isopentyl, 2-methylbutyl, 3-methylbutyl, 2,2-dimethylbutyl, 2,3-dimethylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, -3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, -2-methyl-4-ethylhexyl, 2,2-diethylpentyl, 3,3-diethylhexyl, 2,2-diethylhexyl, 3,3-diethylhexyl.

The term "—($C_2$-$C_{10}$)alkenyl" is intended to mean an unsaturated, linear or branched non-cyclic hydrocarbon-based chain having from 2 to 10 carbon atoms and comprising at least one carbon-carbon double bond. As examples of —($C_1$-$C_{10}$)alkenyl radicals, mention may be made of: 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl.

The term "—($C_2$-$C_{10}$)alkynyl" is intended to mean an unsaturated, linear or branched non-cyclic hydrocarbon-based chain having from 2 to 10 carbon atoms and comprising at least one carbon-carbon triple bond. As examples of —($C_1$-$C_{10}$)alkynyl radicals, mention may be made of: acetylenyl, propynyl, 1-butynyl, 2-butynyl, 1-pentynyl, 2-pentynyl, 3-methyl-1-butynyl, 4-pentynyl, 1-hexynyl, 2-nexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl.

The term "—($C_3$-$C_{10}$)cycloalkyl" is intended to mean a saturated hydrocarbon-based ring having from 3 to 10 carbon atoms. As examples of —($C_3$-$C_{10}$)cycloalkyl radicals, mention may be made of: cyclopropyl, cyclobutyl, cyclopentyl, cyclohexyl, cycloheptyl, cyclooctyl, cyclononyl and cyclodecyl.

The term "—($C_8$-$C_{14}$)bicycloalkyl" is intended to mean a hydrocarbon-based bicycle having from 8 to 14 carbon atoms and at least one saturated cycloalkyl ring. As examples of —($C_8$-$C_{14}$)bicycloalkyl radicals, mention may be made of: indanyle, 1,2,3,4-tetrahydronaphthyl, 5,6,7,8-tetrahydronaphthyl and perhydronaphthyl.

The term "—($C_8$-$C_{14}$)tricycloalkyl" is intended to mean a hydrocarbon-based tricycle having from 8 to 14 carbon atoms and at least one saturated cycloalkyl ring. As examples of —($C_8$-$C_{14}$)tricycloalkyl radicals, mention may be made of: pyrenyl, 1,2,3,4-tetrahydroanthracenyl, perhydroanthracenyl, aceanthrenyl, 1,2,3,4-tetrahydropenanthrenyl, 5,6,7,8-tetrahydrophenanthrenyl and perhydrophenanthrenyl.

The term "—($C_5$-$C_{10}$)cycloalkenyl" is intended to mean a non-aromatic hydrocarbon-based cyclic radical having at least one carbon-carbon double bond in the ring system and from 5 to 10 carbon atoms. As examples of —($C_5$-$C_{10}$)cycloalkenyl radicals, mention may be made of: cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl.

The term "—($C_8$-$C_{14}$)bicycloalkenyl" is intended to mean a hydrocarbon-based bicycle having at least one carbon-carbon double bond in each ring and from 8 to 14 carbon atoms. As examples of —($C_8$-$C_{14}$)bicycloalkenyl radicals, mention may be made of: indenyl, pentalenyl, naphthalenyl, azulenyl, heptalenyl, 1,2,7,8-tetrahydronaphthalenyl.

The term "—($C_8$-$C_{14}$)tricycloalkenyl" is intended to mean a hydrocarbon-based tricycle having at least one carbon-carbon double bond in each ring and from 8 to 14 carbon atoms. As examples of —($C_8$-$C_{14}$)tricycloalkenyl radicals, mention may be made of: anthracenyl, phenalenyl, acenaphthalenyl, as-indacenyl, s-indacenyl.

The term "—($C_{14}$)aryl" is intended to mean an aromatic carbocycle having 14 branches, such as anthryl and phenanthryl.

The term "heterocycle having 3 to 5 branches" is intended to mean a saturated, unsaturated, aromatic or non-aromatic heteromonocycle having 3 to 5 branches having carbon atoms and heteroatoms. A heterocycle having 3 or 4 branches may comprise up to 3 heteroatoms and a heterocycle having 5 branches may comprise up to 4 heteroatoms. Each heteroatom is independently chosen from a nitrogen, possibly quaternized, oxygen, and sulfur, including sulfoxide and sulfone. The heterocycle may be attached via any heteroatom or carbon atom. As examples of heterocycles having 3-5 branches, mention may be made of: furyl, thiophenyl, pyrrolyl, oxazolyl, imidazolyl, thiazolyl, isoxazolyl, pyrazolyl, isothiazolyl, triazinyl, pyrrolidinonyl, pyrrolidinyl, hydantoinyl, oxiranyl, oxetanyl, tetrahydrofuranyl and tetrahydrothiophenyl.

The term "halo" is intended to mean a halogen atom such as F (fluorine), Cl (chlorine), Br (bromine) and I (iodine).

The term "—CH(halo)$_2$" is intended to mean a methyl group in which 2 of the hydrogens are replaced by a halogen atom. Mention may be made, for example, of: —$CHF_2$, —$CHCl_2$, —$CHBr_2$, —CHBrCl, —CHClI and —$CHI_2$.

The term "—CH(halo)$_3$" is intended to mean a methyl group in which 3 of the hydrogens are replaced by a halogen atom. Mention may be made, for example, of: —$CF_3$, —$CF_2Cl$, —$CCl_3$, —$CBr_3$, —$CFB_2$ and —$Cl_3$.

The term "salts of the compounds of formula (I)" is intended to mean a salt formed by an inorganic or organic acid or else an inorganic or organic base.

As examples of acid salts, mention may be made of the sulfate, citrate, acetate, oxalate, chloride, bromide, iodide, nitrate, bisulfate, phosphate, isonicotinate, lactate, salicylate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylenebis(2-hydroxy-3-naphthoate)) salts.

As examples of base salts, mention may be made of hydroxides of alkali metals such as sodium, potassium and lithium; hydroxides of alkaline earth metals such as calcium and magnesium; hydroxides of other metals such as aluminium and zinc; aqueous ammonia and organic amines such as unsubstituted or hydroxy-substituted mono-, di- or trialkylamines; dicyclohexylamines; tributylamines; pyridine; N-methyl-N-ethylamine; diethylamine; triethylamine; mono-, bis- or tris-(2-hydroxyalkylamines) such as mono-, bis- or tris-(2-hydroxyethyl)amine, 2-hydroxy-tert-butylamine or tris-(hydroxymethyl)methylamine, N,N-di-alkyl-N-

(hydroxyalkyl)-amines, such as N,N-dimethyl-N-(2-hydroxyethyl)amine or tri-(2-hydroxyethyl)amine; N-methyl-D-glucamine; and amino acids such as arginine and lysine.

According to a preferred form of the invention, at least one of the radicals $X_1$, $X_2$, $X_3$, $X_4$, $X_5$, $X_a$, $X_b$, $X_c$, $X_d$, $X_e$ and $X_f$ is O.

According to a preferred form of the invention, at least one of the radicals $Y_1$, $Y_2$, $Y_3$, $Y_4$, $Y_5$, $Y_6$, independently denotes H.

According to a preferred form of the invention, at least one of the radicals $Y_1$, $Y_2$, $Y_3$, $Y_4$, $Y_6$, independently denotes $CH_3$.

According to a preferred form of the invention, $R_1$ denotes H or $CH_3$.

According to a preferred form of the invention, n is equal to 5.

According to one particularly preferred form, the compositions of the invention comprise the baicalin corresponding to formula (II) below:

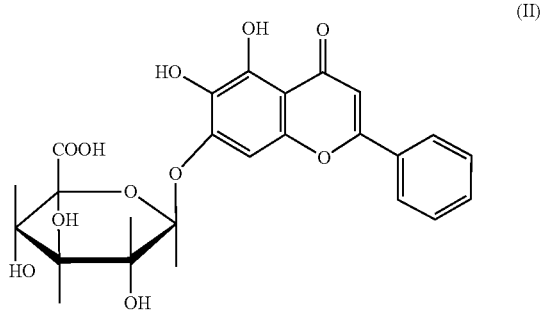 [SMILES: CC1(O)[C@](C)(Oc2cc3oc(-c4ccccc4)cc(=O)c3c(O)c2O)OC2(C(=O)O)O[C@]1(C)[C@]2(C)O]

(II)

or a plant extract comprising same.

This compound is described, in particular, in application WO 2008/140440, especially in the form of a solution. The baicalin may be used in the form of a solution comprising an alkyl glycol having 2 to 7 carbon atoms, a polyol ether, and at least one antioxidant. Such an organic compound may be obtained as described in EP 1 400 579 (US2004/0067894), relating to the synthesis of tetrahydroxyflavones, the general formula of which comprises baicalin.

The baicalin may be used in the form of an extract of plant origin. Baicalin is a polyphenol (flavone) extracted especially from the scullcap root, in particular of *Scutellaria baicalensis*, with the INCI name: *Scutellaria baicalensis* root extract. It originates in traditional Chinese medicine. The various methods for preparing the extracts are described in the application WO 2005/044281.

Baicalin is in particular available from MMP under the trade name Baicalin 95 MM® by MMP.

The baicalin is in the form of a yellow-coloured powder, with a purity optionally greater than 90% or 95%. The baicalin crystals can be in the form of needles. It has very low solubility, in particular in water at spontaneous pH.

Preferentially, the baicalin is included in the cosmetic composition in the completely dissolved state. There are no remaining baicalin crystals visible to the naked eye, under a polarized light microscope or by any technique known to those skilled in the art.

According to one particular embodiment, the baicalin and/or derivatives thereof are present in the compositions according to the invention in active material concentrations ranging from 0.01% to 10% by weight, better still from 0.02% to 8% by weight, even more preferably from 0.1% to 5% by weight relative to the total weight of the composition.

Acrylic Polymers

The composition in accordance with the invention comprises at least one polymer comprising monomer units of formulae (A) and (B):

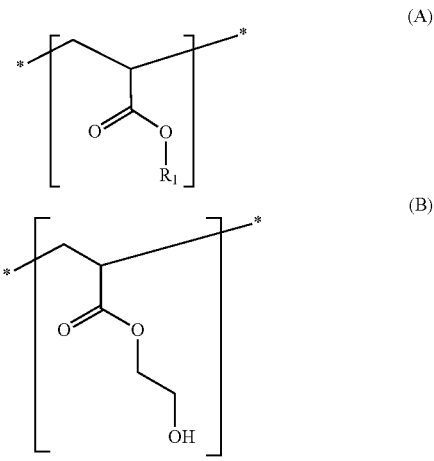

in which:

$R_1$, independently of one another, is chosen from alkyl or alkylene radicals;

and at least 60% by weight of the $R_1$ groups are behenyl radicals, the percentage by weight relating to the sum of all the $R_1$ groups present in the polymer;

and the weight ratio of the sum of all the hydroxyethyl acrylate units to the sum of all the acrylate units bearing the $R_1$ group ranges from 1:30 to 1:1, and the sum of the total of units A and B is at least 95% by weight of the total weight of the polymer.

Preferably, $R_1$ is constituted of alkyl radicals, preferably of $C_{16}$-$C_{22}$ alkyl radicals, and more preferentially of behenyl ($C_{22}$) radicals.

Preferably, at least 70% by weight of the $R_1$ groups are behenyl radicals, preferentially at least 80% by weight, more preferentially at least 90% by weight.

According to a preferred embodiment, all the groups $R_1$ are behenyl radicals.

Preferably, said weight ratio ranges from 1:15 to 1:1, preferentially ranges from 1:10 to 1:4.

Advantageously, the polymer units present in the polymer a) are constituted of the units (A) and (B) previously described.

The polymer a) has a number-average molecular weight Mn ranging from 2000 to 9000 g/mol, preferably ranging from 5000 to 9000 g/mol. The number-average molecular weight can be measured by the gel permeation chromatography method, for example according to the method described in the example hereinbelow.

Preferably, the polymer a) has a melting point ranging from 60° C. to 69° C., and preferentially ranging from 63° C. to 67° C. The melting point is measured by differential scanning calorimetry (DSC), for example according to the method described in the example hereinbelow.

The polymer a) used according to the invention can be prepared by polymerization of a monomer of formula $CH_2$=CH—COO—$R_1$, $R_1$ having the meaning previously described, and of 2-hydroxyethyl acrylate.

The polymerization may be performed according to known methods, such as solution polymerization or emulsion polymerization.

The polymerization is, for example, described in US 2007/0264204.

According to one particular embodiment, the active material concentration of polymers b) according to the invention that are present in the compositions according to the present invention is greater than or equal to 0.1% by weight, better still greater than 0.5% by weight, even better still greater than 1% by weight, preferably greater than 1.5% by weight, relative to the total weight of the composition. Preferably, the active material concentration of polymers b) according to the invention that are present in the compositions according to the present invention is between 0.1% and 10% by weight, better still between 0.5% and 8% by weight, preferably between 1% and 5% by weight, and even more preferentially between 1.5% and 5% by weight, relative to the total weight of the composition.

UV-Screening Agents

According to one particular embodiment, the composition in accordance with the invention comprises at least one UV-screening agent (agent which screens out UV radiation from sunlight). The UV-screening agent(s) can be chosen from organic UV-screening agents and inorganic UV-screening agents.

The term "UV-screening agent" is intended to mean a substance capable of absorbing at least one portion of the UV radiation emitted by the sun, for protecting the skin and/or the lips and/or the hair against the harmful effects of this radiation.

The UV-screening agent is a UV-screening agent normally used in cosmetics. It can be chosen from the positive list contained in Annex VI of Regulation (EC) No 1223/2009, which specifies the list of UV-screening agents authorized in cosmetics.

i) Organic UV-Screening Agents

The organic UV-screening agents are in particular chosen from cinnamic compounds; diphenylacrylate compounds; salicylate compounds; dibenzoylmethane compounds; anthranilate compounds; benzylidenecamphor compounds; benzophenone compounds; triazine compounds; benzotriazole compounds, in particular the silicone benzotriazoles described in patent EP0392883 and the methylenebis(hydroxyphenyl benzotriazole) compounds as described in applications U.S. Pat. Nos. 5,237,071, 5,166,355, GB2303549, DE 197 26 184 and EP893119; benzalmalonate compounds, in particular those mentioned in U.S. Pat. No. 5,624,663; benzimidazole derivatives; imidazoline compounds; the bis-benzoazolyl compounds as described in patents EP669323 and U.S. Pat. No. 2,463,264; the benzoxazole compounds as described in patent applications EP0832642, EP1027883, EP1300137 and DE10162844; screening polymers and screening silicones such as those described in particular in application WO-93/04665; merocyanine compounds as described in U.S. Pat. No. 4,195,999, application WO2004/006878, applications WO2008/090066, WO2011113718, WO2009027258, WO2013010590, WO2013011094, WO2013011480 and the documents IP COM Journal No 000179675D published on 23 Feb. 2009, IP COM Journal No 000182396D published on 29 Apr. 2009, IP COM Journal No 000189542D published on 12 Nov. 2009, and IP COM Journal No IPCOM000011179D published on Apr. 3, 2004, and mixtures thereof.

As examples of organic photoprotective agents, mention may be made of those denoted hereinbelow under their INCI name:

Dibenzoylmethane Compounds
Butyl methoxydibenzoylmethane, sold in particular under the trade name Parsol 1789® by DSM Nutritional Products, Inc.

Cinnamic Compounds:
Ethylhexyl methoxycinnamate, sold in particular under the trade name Parsol MCX® by DSM Nutritional Products,
Isopropyl methoxycinnamate,
Isoamyl p-methoxycinnamate, sold under the trade name Neo Heliopan E 1000° by Symrise, Salicylic Compounds:
Homosalate, sold under the name Eusolex HMS® by Rona/EM Industries,
Ethylhexyl salicylate, sold under the name Neo Heliopan OS® by Symrise,
Dipropylene glycol salicylate, sold under the name Dipsal® by Scher,
TEA salicylate, sold under the name Neo Heliopan TS® by Symrise, β,β-Diphenyl Acrylate Compounds:
Octocrylene, sold in particular under the trade name Uvinul N 539® by BASF,
Etocrylene, sold in particular under the trade name Uvinul N 35® by BASF.

Benzophenone Compounds:
Benzophenone-1, sold under the trade name Uvinul 400® by BASF,
Benzophenone-2, sold under the trade name Uvinul D 50® by BASF,
Benzophenone-3 or Oxybenzone, sold under the trade name Uvinul M 40® by BASF,
Benzophenone-4, sold under the trade name Uvinul MS 40® by BASF,
Benzophenone-5,
Benzophenone-6, sold under the trade name Helisorb 11® by Norquay,
Benzophenone-8, sold under the trade name Spectra-Sorb UV24® by American Cyanamid,
Benzophenone-9, sold under the trade name Uvinul DS 49® by BASF,
Benzophenone-12,
n-Hexyl 2-(4-diethylamino-2-hydroxybenzoyl)benzoate, sold under the trade name Uvinul A Plus® or, as a mixture with octyl methoxycinnamate, under the trade name Uvinul A Plus B® by the company BASF,
1,1'-(1,4-Piperazinediyl)bis[1-[2-[4-(diethylamino)-2-hydroxybenzoyl]phenyl]methanone] (CAS 919803-06-8), as described in patent application WO 2007/071 584; this compound advantageously being used in micronized form (mean size of 0.02 to 2 μm), which may be obtained, for example, according to the micronization process described in patent applications GB-A-2 303 549 and EP-A-893 119, and in particular in the form of an aqueous dispersion.

Benzylidenecamphor Compounds:
3-Benzylidenecamphor, manufactured under the name Mexoryl SD® by Chimex,
4-Methylbenzylidenecamphor, sold under the name Eusolex 6300® by Merck,
Benzylidenecamphorsulfonic acid, manufactured under the name Mexoryl SL® by Chimex,
Camphor benzalkonium methosulfate, manufactured under the name Mexoryl SO® by Chimex,
Terephthalylidenedicamphorsulfonic acid, manufactured under the name Mexoryl SX® by Chimex,
Polyacrylamidomethylbenzylidenecamphor, manufactured under the name Mexoryl SW® by Chimex.

Phenylbenzimidazole Compounds:

Phenylbenzimidazolesulfonic acid, sold in particular under the trade name Eusolex 232® by Merck.

Bis-benzoazolyl Compounds

Disodium phenyl dibenzimidazole tetrasulfonate, sold under the trade name Neo Heliopan AP® by Symrise.

Benzotriazole Compounds

Drometrizole trisiloxane, manufactured under the name Mexoryl SX® by Chimex;

Methylene bis-Benzotriazolyl Tetramethylbutylphenol in particular in solid form, such as the product sold under the trade name MIXXIM BB/100® by Fairmount Chemical or in the form of an aqueous dispersion of micronized particles having a mean particle size which ranges from 0.01 to 5 μm and more preferentially from 0.01 to 2 μm and more particularly from 0.020 to 2 μm, with at least one alkylpolyglycoside surfactant of structure:

$C_nH_{2n+1}O(C_6H_{10}O_5)_xH$ in which n is an integer from 8 to 16 and x is the average degree of polymerization of the $(C_6H_{10}O_5)$ unit and ranges from 1.4 to 1.6, as described in patent GB-A-2 303 549, in particular sold under the trade name Tinosorb M® by the company BASF or in the form of an aqueous dispersion of micronized particles having a mean particle size which ranges from 0.02 to 2 μm and more preferentially from 0.01 to 1.5 μm and more particularly from 0.02 to 1 μm in the presence of at least one mono-$(C_8-C_{20})$alkyl ester of polyglycerol having a degree of glycerol polymerization of at least 5, such as the aqueous dispersions described in application WO 2009/063392.

Triazine Compounds:

Bis-ethylhexyloxyphenol methoxyphenyl triazine, sold under the trade name Tinosorb S® by BASF, Ethylhexyl triazone, sold in particular under the trade name Uvinul T150® by BASF, Diethylhexyl butamido triazone, sold under the trade name Uvasorb HEB® by Sigma 3V, symmetrical triazine screening agents substituted with naphthalenyl groups or polyphenyl groups described in U.S. Pat. No. 6,225,467, patent application WO 2004/085 412 (see compounds 6 and 9) or the document "Symmetrical Triazine Derivatives", IP.COM IPCOM000031257 Journal, INC West Henrietta, N.Y., US (20 Sep. 2004), especially 2,4,6-tris(diphenyl)triazine and 2,4,6-tris(terphenyl)triazine, which is also mentioned in patent applications WO 06/035 000, WO 06/034 982, WO 06/034 991, WO 06/035 007, WO 2006/034 992 and WO 2006/034 985, these compounds advantageously being used in micronized form (mean particle size of 0.02 to 3 μm), which may be obtained, for example, according to the micronization process described in patent applications GB-A-2 303 549 and EP-A-893 119, and especially in aqueous dispersion;

silicone triazines substituted with two aminobenzoate groups, as described in patent EP 0 841 341, in particular 2,4-bis(n-butyl 4'-aminobenzalmalonate)-6-[(3-{1,3,3,3-tetramethyl-1-[(trimethylsilyloxy]disiloxanyl}propyl)amino]-s-triazine.

Anthranilic Compounds:

Menthyl anthranilate, sold under the trade name Neo Heliopan MA® by Symrise.

Imidazoline Compounds:

Ethylhexyl dimethoxybenzylidene dioxoimidazoline propionate,

Benzalmalonate Compounds:

Polyorganosiloxane containing benzalmalonate functional groups, for instance Polysilicone-15, sold under the trade name Parsol SLX® by DSM Nutritional Products, Inc.

Benzoxazole Compounds:

2,4-Bis[5-(1,1-dimethylpropyl)benzoxazol-2-yl(4-phenyl)imino]-6-(2-ethylhexyl)imino-1,3,5-triazine, sold under the name Uvasorb K2A® by Sigma 3V.

ii) Mineral UV-Screening Agents

The mineral UV-screening agents used in accordance with the present invention are metal oxide pigments. More preferentially, the inorganic UV-screening agents of the invention are metal oxide particles with a mean elementary particle size of less than or equal to 0.5 μm, more preferentially between 0.005 and 0.5 μm, even more preferentially between 0.01 and 0.2 μm, better still between 0.01 and 0.1 μm and more particularly between 0.015 and 0.05 μm.

They may be chosen in particular from titanium oxide, zinc oxide, iron oxide, zirconium oxide and cerium oxide, or mixtures thereof.

Such coated or uncoated metal oxide pigments are described in particular in patent application EP-A-0 518 773. Commercial pigments that may be mentioned include the products sold by the companies Sachtleben Pigments, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

The coated pigments are more particularly titanium oxides that have been coated:

with silica, such as the product Sunveil® from the company Ikeda, with silica and iron oxide, such as the product Sunveil F® from the company Ikeda, with silica and alumina, such as the products Microtitanium Dioxide MT 500 SA® and Microtitanium Dioxide MT 100 SA from the company Tayca and Tioveil from the company Tioxide, with alumina, such as the products Tipaque TTO-55 (B)® and Tipaque TTO-55 (A)® from the company Ishihara and UVT 14/4 from the company Sachtleben Pigments, with alumina and aluminium stearate, such as the products Microtitanium Dioxide MT 100 T®, MT 100 TX®, MT 100 Z° and MT-01® from the company Tayca, the products Solaveil CT-10 W® and Solaveil CT 100® from the company Uniqema and the product Eusolex T-AVO® from the company Merck, with silica, alumina and alginic acid, such as the product MT-100 AQ® from the company Tayca, with alumina and aluminium laurate, such as the product Microtitanium Dioxide MT 100 S® from the company Tayca, with iron oxide and iron stearate, such as the product Microtitanium Dioxide MT 100 F® from the company Tayca, with zinc oxide and zinc stearate, such as the product BR 351® from the company Tayca, with silica and alumina and treated with a silicone, such as the products Microtitanium Dioxide MT 600 SAS®, Microtitanium Dioxide MT 500 SAS® or Microtitanium Dioxide MT 100 SAS® from the company Tayca, with silica, alumina and aluminium stearate and treated with a silicone, such as the product STT-30-DS® from the company Titan Kogyo, with silica and treated with a silicone, such as the product UV-Titan X 195® from the company Sachtleben Pigments, with alumina and treated with a silicone, such as the products Tipaque TTO-55 (S)® from the company Ishihara or UV Titan M 262® from the company Sachtleben Pigments, with triethanolamine, such as the product STT-65-S from the company Titan Kogyo, with stearic acid, such as the product Tipaque TTO-55 (C)® from the company Ishihara, with sodium hexametaphosphate, such as the product Microtitanium Dioxide MT 150 W® from the company Tayca, $TiO_2$ treated with octyltrimethylsilane, sold under the trade name T 805® by the company Degussa Silices, $TiO_2$ treated with a polydimethylsiloxane, sold under the trade name 70250 Cardre UF TiO2SI3® by the company Cardre, anatase/rutile $TiO_2$ treated with a polydimethylhydrogenosiloxane, sold under the trade name Micro Titanium Dioxide USP Grade Hydrophobic® by the company Color Techniques.

Mention may also be made of $TiO_2$ pigments doped with at least one transition metal such as iron, zinc or manganese and more particularly manganese.

Preferably, said doped pigments are in the form of an oily dispersion. The oil present in the oily dispersion is preferably chosen from triglycerides including those of capric/caprylic acids. The oily dispersion of titanium oxide particles may also comprise one or more dispersants, for instance a sorbitan ester, for instance sorbitan isostearate, or a polyoxyalkylenated fatty acid ester of glycerol, for instance TRI-PPG-3 myristyl ether citrate and polyglyceryl-3 polyricinoleate. Preferably, the oily dispersion of titanium oxide particles comprises at least one dispersant chosen from polyoxyalkylenated fatty acid esters of glycerol. Mention may be made more particularly of the oily dispersion of $TiO_2$ particles doped with manganese in capric/caprylic acid triglyceride in the presence of TRI-PPG-3 myristyl ether citrate and polyglyceryl-3 polyricinoleate and sorbitan isostearate having the INCI name: titanium dioxide (and) TRI-PPG-3 myristyl ether citrate (and) polyglyceryl-3 ricinoleate (and) sorbitan isostearate, for instance the product sold under the trade name Optisol TD50® by the company Croda.

The uncoated titanium oxide pigments are sold, for example, by the company Tayca under the trade names Microtitanium Dioxide MT 500 B or Microtitanium Dioxide MT 600 B®, by the company Degussa under the name P 25, by the company Wacker under the name Transparent titanium oxide PW®, by the company Miyoshi Kasei under the name UFTRO, by the company Tomen under the name ITS® and by the company Tioxide under the name Tioveil AQ.

The uncoated zinc oxide pigments are, for example:
those sold under the name Z-Cote by the company Sunsmart;
those sold under the name Nanox® by the company Elementis;
those sold under the name Nanogard WCD 2025® by the company Nanophase Technologies.

The coated zinc oxide pigments are, for example:
those sold under the name Zinc Oxide CS-5® by the company Toshibi (ZnO coated with polymethylhydrogenosiloxane);

those sold under the name Nanogard Zinc Oxide FN® by the company Nanophase Technologies (as a 40% dispersion in Finsolv TN®, $C_{12}$-$C_{15}$ alkyl benzoate);

those sold under the name Daitopersion Zn-30® and Daitopersion Zn-50® by Daito (dispersions in cyclopolymethylsiloxane/oxyethylenated polydimethylsiloxane, containing 30% or 50% of zinc oxides coated with silica and polymethylhydrogenosiloxane);

those sold under the name NFD Ultrafine ZnO® by the company Daikin (ZnO coated with perfluoroalkyl phosphate and copolymer based on perfluoroalkylethyl as a dispersion in cyclopentasiloxane);

those sold under the name SPD-Z1® by the company Shin-Etsu (ZnO coated with silicone-grafted acrylic polymer, dispersed in cyclodimethylsiloxane);

those sold under the name Escalol Z100® by the company ISP (alumina-treated ZnO dispersed in the ethylhexyl methoxycinnamate/PVP-hexadecene copolymer/methicone mixture);

those sold under the name Fuji ZnO-SMS-10® by the company Fuji Pigment (ZnO coated with silica and polymethylsilsesquioxane);

those sold under the name Nanox Gel TN® by the company Elementis (ZnO dispersed at a concentration of 55% in $C_{12}$-$C_{15}$ alkyl benzoate with hydroxystearic acid polycondensate).

The uncoated cerium oxide pigments may be, for example, those sold under the name Colloidal Cerium Oxide® by the company Rhône-Poulenc.

The uncoated iron oxide pigments are sold, for example, by the company Arnaud under the names Nanogard WCD 2002® (FE 45B®), Nanogard Iron FE 45 BL AQ, Nanogard FE 45R AQ® and Nanogard WCD 2006® (FE 45R®) or by the company Mitsubishi under the name TY-220®.

The coated iron oxide pigments are sold, for example, by the company Arnaud under the names Nanogard WCD 2008 (FE 45B FN)®, Nanogard WCD 2009® (FE 45B 556®), Nanogard FE 45 BL 345® and Nanogard FE 45 BL® or by the company BASF under the name Transparent Iron Oxide®.

Mention may also be made of mixtures of metal oxides, especially of titanium dioxide and of cerium dioxide, including the equal-weight mixture of titanium dioxide and cerium dioxide coated with silica, sold by the company Ikeda under the name Sunveil A®, and also the mixture of titanium dioxide and zinc dioxide coated with alumina, silica and silicone, such as the product M 261® sold by the company Sachtleben Pigments, or coated with alumina, silica and glycerol, such as the product M 211® sold by the company Sachtleben Pigments.

According to the invention, the coated or uncoated mineral screening agents based on titanium oxide are particularly preferred.

According to one particular embodiment, the UV-screening agent or agents are present in the compositions according to the invention in an active material content ranging from 0.1% to 45% by weight and in particular from 5% to 35% by weight, relative to the total weight of the composition.

The compositions according to the invention may comprise at least one aqueous phase.

The aqueous phase contains water and optionally other water-soluble or water-miscible organic solvents.

An aqueous phase that is suitable for use in the invention may comprise, for example, a water chosen from a natural spring water, such as water from La Roche-Posay, water from Lucas, water from Vittel or waters from Vichy, or a floral water.

The aqueous phase may comprise at least one hydrophilic solvent, such as, for example, substantially linear or branched lower monoalcohols having from 1 to 8 carbon atoms, such as ethanol, propanol, butanol, isopropanol or isobutanol; polyols, such as propylene glycol, isoprene glycol, butylene glycol, caprylyl glycol, glycerol, sorbitol, polyalkylene glycols such as polyethylene glycols, and mixtures thereof.

According to one particular embodiment of the invention, the weight concentrations of hydrophilic solvents range from 0.01% to 40% by weight relative to the total weight of said composition.

Preferably, the weight concentrations of hydrophilic solvents range from 0.1% to 30%, and preferably from 5% to 20%, by weight relative to the total weight of said composition.

Depending on the presentation form of the composition, the amount of aqueous phase may range from 0.1% to 99% by weight, preferably from 0.5% to 98% by weight, better still from 30% to 95% by weight and even better still from 40% to 95% by weight relative to the total weight of the composition.

Depending on the fluidity of the composition that it is desired to obtain, one or more additional gelling agents, other than the polymers b) as previously described, which are in particular hydrophilic, that is to say water-soluble or water-dispersible, can be incorporated.

Examples of hydrophilic gelling agents that may be mentioned include modified or unmodified carboxyvinyl polymers, such as the products sold under the names Carbopol (CTFA name: carbomer) and Pemulen (CTFA name: Acrylates/C10-30 alkyl acrylate crosspolymer) by the company Goodrich; polyacrylamides; optionally crosslinked and/or neutralized 2-acrylamido-2-methylpropane sulfonic acid polymers and copolymers, for instance the poly(2-acrylamido-2-methylpropanesulfonic acid) sold by the company Hoechst under the name "Hostacerin AMPS" (CTFA name: Ammonium polyacryldimethyltauramide); crosslinked anionic copolymers of acrylamide and of AMPS, which are in the form of a W/O emulsion, such as those sold under the name Sepigel 305 (CTFA name: Polyacrylamide/C13-14 isoparaffin/Laureth-7) and under the name Simulgel 600 (CTFA name: Acrylamide/Sodium acryloyldimethyltaurate copolymer/Isohexadecane/Polysorbate 80) by the company SEPPIC; polysaccharide biopolymers, for instance xanthan gum, guar gum, alginates and modified celluloses; and mixtures thereof. The amount of gelling agents depends on the desired objective. According to one embodiment, the amount of gelling agents ranges for example from 0.001% to 10% and for example from 0.1% to 5% by weight, relative to the total weight of the composition.

When the composition used according to the invention comprises an oily phase, it preferably contains at least one oil, in particular one cosmetic oil. It may also contain other fatty substances.

As oils that may be used in the composition of the invention, mention may be made, for example, of:
- hydrocarbon-based oils of animal origin, such as perhydrosqualene;
- hydrocarbon-based oils of plant origin, such as liquid fatty acid triglycerides containing from 4 to 10 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol 810, 812 and 818 by the company Dynamit Nobel, jojoba oil and shea butter oil;
- synthetic esters and ethers, especially of fatty acids, for instance the oils of formulae R1COOR2 and R1OR2 in which $R_1$ represents the residue of a fatty acid containing from 8 to 29 carbon atoms and R2 represents a branched or unbranched hydrocarbon-based chain containing from 3 to 30 carbon atoms, for instance Purcellin oil, isononyl isononanoate, isopropyl myristate, 2-ethylhexyl palmitate, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate or triisocetyl citrate; fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate;
- linear or branched hydrocarbons of mineral or synthetic origin, such as volatile or non-volatile liquid paraffins, and derivatives thereof, hydrocarbon-based oils having a branched chain comprising from 10 to 20 carbon atoms, such as isohexadecane, isododecane, isoparaffins and mixtures thereof, petroleum jelly, polydecenes, and hydrogenated polyisobutene such as Parleam Oil®;
- natural or synthetic essential oils, for instance eucalyptus oil, hybrid lavender oil, lavender oil, vetiver oil, litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil;
- fatty alcohols and fatty acids containing from 8 to 26 carbon atoms, for instance cetyl alcohol or acid, stearyl alcohol, stearic acid, a mixture of cetyl alcohol and of stearyl alcohol (cetylstearyl alcohol), octyldodecanol, 2-butyloctanol, 2-hexyldecanol, 2-undecylpentadecanol, oleyl alcohol or linoleyl alcohol;
- partially hydrocarbon-based and/or silicone-based fluoro oils, such as those described in document JP-A-2-295 912;
- silicone oils, such as volatile or non-volatile polydimethylsiloxanes (PDMS) with a linear or cyclic silicone chain, which are liquid or pasty at ambient temperature, especially cyclopolydimethylsiloxanes (cyclomethicones) such as cyclohexasiloxane; polydimethylsiloxanes comprising alkyl, alkoxy or phenyl groups, which are pendent or at the end of a silicone chain, groups having from 2 to 24 carbon atoms; phenylsilicones, such as phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes;
- mixtures thereof.

In the list of oils mentioned above, "hydrocarbon-based oil" is intended to mean any oil predominantly comprising carbon and hydrogen atoms, and optionally ester, ether, fluoro, carboxylic acid and/or alcohol groups.

The other fatty substances that may be present in the oily phase are, for example, fatty acids comprising from 8 to 30 carbon atoms, such as stearic acid, lauric acid, palmitic acid and oleic acid; waxes, such as lanolin wax, beeswax, carnauba wax or candelilla wax, paraffin waxes, lignite wax or microcrystalline waxes, ceresin or ozokerite, and synthetic waxes, such as polyethylene waxes and Fischer-Tropsch waxes; silicone resins such as trifluoromethyl-$C_1$-$C_4$-alkyl dimethicone and trifluoropropyl dimethicone; and silicone elastomers, such as the products sold under the name KSG by the company Shin-Etsu, under the names Trefil, BY29 or EPSX by the company Dow Corning, or under the name Gransil by the company Grant Industries.

These fatty substances may be chosen in a varied manner by those skilled in the art in order to prepare a composition having the desired properties, for example in terms of consistency or texture.

According to one variant, the amount of oily phase can range for example from 0.01% to 60% and for example from 5% to 50% by weight, relative to the total weight of the composition.

According to one variant, the amount of oily phase can range for example from 10% to 40% by weight, relative to the total weight of the composition.

According to a particular embodiment, the compositions in accordance with the invention comprise an aqueous phase. In particular, the compositions in accordance with the invention may be aqueous or aqueous-alcoholic solutions.

According to another embodiment, the composition according to the invention is in the form of an emulsion. It can then also comprise at least one emulsifier.

When the composition according to the invention is a water-in-oil (W/O) or oil-in-water (O/W) emulsion, the proportion of the oily phase of the emulsion can range from 5% to 80% by weight, and preferably from 5% to 50% by weight, relative to the total weight of the composition. The emulsions generally contain at least one emulsifier chosen from amphoteric, anionic, cationic and non-ionic emulsifiers, used alone or as a mixture, and optionally a co-emulsifier. The emulsifiers are chosen in an appropriate manner according to the emulsion to be obtained (W/O or O/W emulsion). The emulsifier and the co-emulsifier are generally present in the composition in a proportion possibly ranging for example from 0.3% to 30% by weight and preferably from 0.5% to 20% by weight relative to the total weight of the composition.

For the W/O emulsions, examples of emulsifiers that may be mentioned include dimethicone copolyols such as the mixture of cyclomethicone and of dimethicone copolyol sold under the name DC 5225 C by the company Dow Corning, and alkyl dimethicone copolyols such as the laurylmethicone copolyol sold under the name Dow Corning 5200 Formulation Aid by the company Dow Corning and the cetyl dimethicone copolyol sold under the name Abil EM 90R by the company Goldschmidt, or the mixture polyglyceryl-4 isostearate/cetyl dimethicone copolyol/hexyl laurate sold under the name Abil WE 09 by the company Goldschmidt. One or more co-emulsifiers may also be added thereto. The co-emulsifier may be advantageously chosen from the group comprising polyol alkyl esters. Polyol alkyl esters that may especially be mentioned include glycerol and/or sorbitan esters, for example polyglyceryl isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and any one of the mixtures thereof.

A crosslinked elastomeric solid organopolysiloxane comprising at least one oxyalkylene group, such as those obtained according to the procedure of Examples 3, 4 and 8 of document U.S. Pat. No. 5,412,004 and of the examples of document U.S. Pat. No. 5,811,487, especially the product of Example 3 (synthesis example) of U.S. Pat. No. 5,412,004, and such as the product sold under the reference KSG 21 by the company Shin-Etsu, may also be used as surfactant for W/O emulsions.

Examples of emulsifiers that may be mentioned for the O/W emulsions include non-ionic surfactants, and especially esters of polyols and of fatty acids with a saturated or unsaturated chain containing, for example, from 8 to 24 carbon atoms and better still from 12 to 22 carbon atoms, and the oxyalkylenated derivatives thereof, i.e. derivatives containing oxyethylenated and/or oxypropylenated units, such as the glyceryl esters of $C_8$-$C_{24}$ fatty acids, and the oxyalkylenated derivatives thereof; the polyethylene glycol esters of $C_8$-$C_{24}$ fatty acids, and the oxyalkylenated derivatives thereof; the sorbitol esters of $C_8$-$C_{24}$ fatty acids, and the oxyalkylenated derivatives thereof; the sugar (sucrose, glucose or alkylglucose) esters of $C_8$-$C_{24}$ fatty acids, and the oxyalkylenated derivatives thereof; fatty alcohol ethers; the sugar ethers of $C_8$-$C_{24}$ fatty alcohols, and the any one of mixtures thereof.

Glyceryl esters of fatty acids that may especially be mentioned include glyceryl stearate (glyceryl monostearate, distearate and/or tristearate) (CTFA name: glyceryl stearate) or glyceryl ricinoleate, and mixtures thereof.

Polyethylene glycol esters of fatty acids that may especially be mentioned include polyethylene glycol stearate (polyethylene glycol monostearate, distearate and/or tristearate) and more especially polyethylene glycol 50 OE monostearate (CTFA name: PEG-50 stearate) and polyethylene glycol 100 OE monostearate (CTFA name: PEG-100 stearate), and mixtures thereof.

Mixtures of these surfactants may also be used, for instance the product containing glyceryl stearate and PEG-100 stearate, sold under the name Arlacel 165 by the company Uniqema, and the product containing glyceryl stearate (glyceryl mono-distearate) and potassium stearate, sold under the name Tegin by the company Goldschmidt (CTFA name: glyceryl stearate SE). Fatty acid esters of glucose or of alkyl glucose that may be mentioned in particular include glucose palmitate, alkyl glucose sesquistearates, for instance methyl glucose sesquistearate, alkyl glucose palmitates, for instance methyl glucose palmitate or ethyl glucose palmitate, fatty esters of methyl glucoside and more especially the diester of methyl glucoside and of oleic acid (CTFA name: methyl glucose dioleate); the mixed ester of methyl glucoside and of the oleic acid/hydroxystearic acid mixture (CTFA name: methyl glucose dioleate/hydroxystearate); the ester of methyl glucoside and of isostearic acid (CTFA name: methyl glucose isostearate); the ester of methyl glucoside and of lauric acid (CTFA name: methyl glucose laurate); the mixture of the monoester and diester of methyl glucoside and of isostearic acid (CTFA name: methyl glucose sesquiisostearate); the mixture of the monoester and diester of methyl glucoside and of stearic acid (CTFA name: methyl glucose sesquistearate) and in particular the product sold under the name Glucate SS by the company Amerchol, and mixtures thereof.

Examples of oxyethylenated ethers of a fatty acid and of glucose or of alkyl glucose that may be mentioned include the oxyethylenated ethers of a fatty acid and of methyl glucose, and in particular the polyethylene glycol ether of the diester of methyl glucose and of stearic acid containing about 20 mol of ethylene oxide (CTFA name: PEG-20 methyl glucose distearate), such as the product sold under the name Glucam E-20 distearate by the company Amerchol; the polyethylene glycol ether of the mixture of monoester and diester of methyl glucose and of stearic acid containing about 20 mol of ethylene oxide (CTFA name: PEG-20 methyl glucose sesquistearate) and in particular the product sold under the name Glucamate SSE-20 by the company Amerchol, and the product sold under the name Grillocose PSE-20 by the company Goldschmidt, and mixtures thereof.

Examples of sucrose esters that may be mentioned include sucrose palmitostearate, sucrose stearate and sucrose monolaurate. Examples of fatty alcohol ethers that may be mentioned include polyethylene glycol ethers of fatty alcohols including from 8 to 30 carbon atoms and in particular from 10 to 22 carbon atoms, such as polyethylene glycol ethers of cetyl alcohol, of stearyl alcohol or of cetearyl alcohol (mixture of cetyl alcohol and stearyl alcohol). Mention may be made, for example, of ethers including from 1 to 200 and preferably from 2 to 100 oxyethylene groups, such as those with the CTFA name Ceteareth-20 or Ceteareth-30, and mixtures thereof.

Sugar ethers that may especially be mentioned are alkyl polyglucosides, for example decyl glucoside, for instance the product sold under the name Mydol 10 by the company Kao Chemicals, the product sold under the name Plantaren 2000 by the company Henkel, and the product sold under the name Oramix NS 10 by the company SEPPIC; caprylyl/capryl glucoside, for instance the product sold under the name Oramix CG 110 by the company SEPPIC or under the name Lutensol GD 70 by the company BASF; lauryl glucoside, for instance the products sold under the names Plantaren 1200 N and Plantacare 1200 by the company Henkel; coco glucoside, for instance the product sold under the name Plantacare 818/UP by the company Henkel; cetostearyl glucoside optionally as a mixture with cetostearyl alcohol, sold, for example, under the name Montanov 68 by the company SEPPIC, under the name Tego-Care CG90 by the company Goldschmidt and under the name Emulgade KE3302 by the company Henkel, and also arachidyl glucoside, for example in the form of the mixture of arachidyl alcohol and behenyl alcohol and arachidyl glucoside, sold under the name Montanov 202 by the company SEPPIC and any one of the mixtures thereof.

According to one particular embodiment, the concentration of the emulsifiers in the composition according to the invention ranges from 0.001% to 20%, preferably from 0.5% to 10% by weight, relative to the total weight of the composition.

According to one particular embodiment, the composition in accordance with the invention is in the form of an emulsion or in the form of a gel. When it is present in the form of an emulsion, it may be in the form of a direct (oil-in-water) emulsion or an inverse (water-in-oil) emulsion. Preferably, the composition in accordance with the invention is in the form of a direct (oil-in-water) emulsion.

The composition in accordance with the invention may also comprise at least one fragrance.

When the composition comprises fragrance(s), the amount thereof can range for example from 0.001% to 10% and preferably from 0.01% to 5% by weight, relative to the total weight of the composition.

The composition according to the invention may also comprise at least one preservative.

Advantageously, the preservative(s) are chosen from the preservatives normally used in cosmetics. They can in particular be chosen from the positive list contained in Annex V of Regulation (EC) No 1223/2009, which specifies the list of preservatives authorized in cosmetics.

When the composition comprises one or more preservatives, they are present in a weight concentration of from 0.001% to 10%, preferably from 0.1% to 2%, relative to the total weight of the composition.

Needless to say, those skilled in the art will take care to select the optional adjuvant(s) added to the composition according to the invention such that the advantageous properties intrinsically associated with the composition in accordance with the invention are not, or are not substantially, adversely affected by the envisioned addition.

The examples that follow will allow the invention to be understood more clearly, without, however, being limiting in nature. The amounts indicated are weight percentages of starting material, unless otherwise mentioned. The names of the compounds are given as the INCI names.

EXAMPLES

Example of Preparation of Polymer 1

Determination of the molecular weight by gel permeation chromatography (GPC):

The sample is prepared by preparing a solution of the polymer at 10 mg/ml in tetrahydrofuran. The sample is placed in an oven at 54° C. for 10 minutes and then in an oscillating shaker for 60 minutes to aid dissolution. After visual inspection, the sample appears to be totally dissolved in the solvent.

The sample prepared was analysed using two polypore 300×7.5 mm columns (manufactured by Agilent Technologies), a Waters 2695 chromatographic system, a tetrahydrofuran mobile phase and detection by refractive index. The sample was filtered through a 0.45 µm nylon filter, before being injected into the liquid chromatograph. The standards used for the calibration are the Easi Vial narrow polystyrene (PS) standards from Agilent Technologies.

Polystyrene standards ranging from 2 520 000 to 162 daltons were used for the calibration.

The system is equipped with a PSS SECcurity 1260 RI detector. The polystyrene calibration curve was used to determine the average molecular weight. The recording of the diagrams and the determination of the various molecular weights were performed by the Win GPC Unichrom 81 program.

Determination of the melting point by differential scanning calorimetry (or DSC):

This method describes the general procedure for determining the melting point of polymers by differential scanning calorimetry. This method is based on the standards ASTM E791 and ASTM D 34182 and the DSC calibration is performed according to standard ASTM E 9672.

Behenyl Acrylate/2-Hydroxyethyl Acrylate Copolymer (Polymer 1):

In a 4-necked flask equipped with a side-blade mixer, an internal thermometer, two funnels, a reflux condenser, and an extension for two other necks, 175 g of behenyl acrylate, 25 g of 2-hydroxyethyl acrylate and 0.4 g of 2,2'-azobis(2-methylbutyronitrile) (Akzo Nobel) were added, over the course of 60 minutes at 80° C., to 40 g of isopropanol, with stirring, after having removed the oxygen from the system by means of a nitrogen flush for 20 minutes. The mixture was stirred at 80° C. for 3 hours. The solvent was then eliminated by vacuum distillation, then 1 g of dilauryl peroxide was added and the reaction was continued for 60 minutes at 110° C. The step was repeated. The mixture was then cooled to 90° C., a stream of demineralized water was added and the mixture was then stirred. The water was removed by vacuum distillation.

Molecular weight: Mn=7300 g/mol, Mw=21 000, Mw/Mn=2.8

Melting point: 65° C.

In the examples which follow, for each composition, the viscosity was measured, the stability over time at two months at 45° C. was observed, and then the sensory aspect was evaluated during and after the application of said composition to the skin. For each composition comprising a UV-screening agent, the in vitro SPF value was also measured.

Viscosity Measurement

The viscosity measurement is generally carried out at 25° C., using a Rheomat RM180® viscometer equipped with a No. 3 spindle, the measurement being carried out after 10 minutes of rotation of the spindle in the composition (after which time stabilization of the viscosity and of the speed of rotation of the spindle are observed), at a shear rate of 200 $s^{-1}$.

Protocol for Evaluating the Tack

The tack is evaluated by a panel of sensory experts made up of 10 individuals. Each composition is applied to the forearm at a dose of 2 mg/cm². The product was spread by circular movements until it had penetrated (approximately 30 seconds). The tack is evaluated after 2 minutes of drying, by applying the back of the hand to the treated area, according to a scale ranging from 1 to 15 in which 1 constitutes a very tacky reference and 15 constitutes a non-tacky reference.

Yellowing Measurements:

The colour of the formulae was evaluated after preparation of thin films on a contrast card. The formulae are deposited inside a circle 2.2 cm in diameter, and are spread level in order to obtain reproducible deposit thicknesses. The colorimetric measurements are then carried out by means of a Minolta CM2600D spectrocolorimeter at two points of the film. This operation is reproduced twice, which results in 4 experimental values per composition.

The results are expressed in the (L*, a*, b*) system, in which L* represents the luminance, a* represents the red-green axis (−a*=green, +a*=red) and b* represents the yellow-blue axis (−b*=blue, +b*=yellow). Thus, a* and b* express the hue of the compound. The value of chroma (C*) is calculated in the CIE L*a*b* system according to the formula C*=((e)^2+(b*)^2)^0.5.

The higher the value of chroma C*, the more marked is the intensity of the colour of the product.

In vitro SPF

The sun protection factor (SPF) is determined according to the "in vitro" method described by B. L. Diffey in J. Soc. Cosmet. Chem. 40, 127-133, (1989). The measurements were taken by means of a UV-2000S spectrophotometer from the company Labsphere. Each composition is applied to a rough plate of PMMA, in the form of a uniform and even deposit in a proportion of 1.3 mg/cm².

Examples 1 to 3: Compositions in O/W Emulsion Form

The following compositions were prepared.

| Phases | Composition (% by weight) | 1 (invention) | 2 (comparative) | 3 (comparative) |
|---|---|---|---|---|
| A1 | WATER | qs 100 | qs 100 | qs 100 |
| A1 | EDTA | 0.1 | 0.1 | 0.1 |
| A1 | GLYCEROL | 5 | 5 | 5 |
| A2 | WATER | 8 | 8 | 8 |
| A2 | SCUTELLARIA BAICALENSIS EXTRACT (BAICALIN 95 MM sold by MMP) | 0.25 | 0.25 | 0.25 |
| A2 | TRIETHANOLAMINE | 0.17 | 0.17 | 0.17 |
| B | Polymer 1 | 2 | — | |
| B | Polystearyl acrylate (INTELIMER IPA 13-1 from AIR PRODUCT) | | 2 | |
| B | DICAPRYLYL CARBONATE (CETIOL CC from COGNIS) | 5 | 5 | 5 |
| B | ISONONYL ISONONANOATE | 2.5 | 2.5 | 2.5 |
| B | DIMETHICONE (Viscosity: 5 cSt) | 5 | 5 | 5 |
| B | GLYCERYL STEARATE (and) PEG-100 STEARATE (ARLACEL 165 from CRODA) | 2 | 2 | 2 |
| B | CETYL ALCOHOL | 1 | 1 | 1 |
| B | BUTYL METHOXYDIBENZOYLMETHANE | 2 | 2 | 2 |
| B | OCTOCRYLENE | 6 | 6 | 6 |
| B | PARAFFIN WAX (SASOLWAX 5603 from SASOL) | 0.5 | 0.5 | 0.5 |
| B | VITAMIN E | 1 | 1 | 1 |
| C | AMMONIUM ACRYLOYLDIMETHYLTAURATE/ VP COPOLYMER (95% AM) (ARISTOFLEX AVC from CLARIANT) | 1.23 AM | 1.23 AM | 1.23 AM |
| D | TALC | 2 | 2 | 2 |
| E | CITRIC ACID at 5% in water qs | pH = 5.5 ± 0.3 | pH = 5.5 ± 0.3 | pH = 5.5 ± 0.3 |

Preparation of the Compositions

The starting materials are first weighed out carefully using a balance (precision=0.01 g).

The components of phase A1 are heated to 70° C. using a hotplate, and are mixed using a Rayneri blender.

Phase A2 is then introduced into phase A1 at 70° C. with stirring using a Rayneri blender, until a homogeneous clear mixture is obtained.

Phase B is heated to 70° C., then introduced into phase A1+A2. The emulsification is carried out at 70° C. using a rotor-stator of Moritz type. After 10 minutes of emulsion, the preparation is brought back to ambient temperature.

Phase C is introduced into the emulsion obtained, with Rayneri stirring at ambient temperature.

Phase D is introduced into the preparation.

The pH is adjusted at the end of formulation using 5% citric acid in water constituting phase E, to pH=5.5±0.3.

The following results were obtained:

|  |  | 1 (invention) | 2 | 3 |
|---|---|---|---|---|
| Viscosity | | 14.8 P | 12.8 P | 10.2 P |
| Stability after 2 months at 45° C. | | YES | YES | YES |
| in vitro SPF | | 11.2 ± 0.8 | 8.4 ± 0.8 | 6.1 ± 0.5 |
| Mattness (Score by sensory expert panel, out of 15; 1 = Shiny; 15 = Non-shiny) | | 10.1 ± 1.4 | 4.8 ± 0.6 | 2.1 ± 0.2 |
| Tack (Score by sensory expert panel, out of 15; 1 = Very tacky; 15 = Non-tacky) | | 10.8 ± 1.1 | 5.0 ± 0.9 | 4.9 ± 1 |
| Non-greasy finish (Score by sensory expert panel, out of 15; 1 = Greasy finish; 15 = Non-greasy finish) | | 9.1 ± 1.9 | 8.1 ± 1.9 | 5.1 ± 1.1 |
| Colorimetric evaluation of the compositions | L* | 91.4 | 92.1 | 91.6 |
| | a* | −1.2 | −4.9 | −4.8 |
| | b* | 3.6 | 9.8 | 10.4 |
| | C* | 3.8 | 11 | 11.5 |
| | Colour | Pale yellow | Very yellow | Very yellow |

As demonstrated by the results of Compositions 2 and 3 (comparative compositions), a formula comprising baicalin and a lipophilic polymer outside the invention has a very strong yellow colouration and leads to high shininess and a greasy finish.

Conversely, Composition 1 (invention) with a polymer according to the invention is less yellow and provides a matt and non-greasy finish.

Examples 4 and 5

The following compositions according to the invention were prepared.

| Phases | Composition (% by weight) | 4 (invention) | 5 (invention) |
|---|---|---|---|
| A1 | WATER | qs 100 | qs 100 |
| A1 | EDTA | 0.1 | 0.1 |
| A1 | GLYCEROL | 5 | 5 |
| A2 | WATER | 8 | 8 |
| A2 | SCUTELLARIA BAICALENSIS EXTRACT (BAICALIN 95 MM sold by MMP) | 0.25 | 1 |
| A2 | TRIETHANOLAMINE | 0.17 | 0.17 |
| A3 | ACRYLATES COPOLYMER (CARBOPOL AQUA SF1 POLYMER from LUBRIZOL) (30% AM) | 0.6 AM | 0.6 AM |
| A3 | TRIETHANOLAMINE | 0.25 | 0.25 |
| A3 | WATER | 5 | 5 |
| B | Polymer 1 | 4 | 4 |
| B | DICAPRYLYL CARBONATE (CETIOL CC from COGNIS) | 5 | 5 |
| B | ISONONYL ISONONANOATE | 2.5 | 2.5 |
| B | DIMETHICONE (Viscosity: 5 cSt) | 5 | 5 |
| B | GLYCERYL STEARATE (and) PEG-100 STEARATE (ARLACEL 165 from CRODA) | 2 | 2 |
| B | CETYL ALCOHOL | 1 | 1 |
| B | BUTYL | 2 | 2 |
| M | ETHOXYDI BENZOYLMETHANE | | |
| B | OCTOCRYLENE | 6 | 6 |
| B | PARAFFIN WAX (SASOLWAX 5603 from SASOL) | 0.5 | 0.5 |
| B | VITAMIN E | 1 | 1 |
| C | AMMONIUM ACRYLOYLDIMETHYLTAURATE/ VP COPOLYMER (95% AM) (ARISTOFLEX AVC from CLARIANT) | 1.23 AM | 1.23 AM |
| D | TALC | 2 | 2 |
| E | CITRIC ACID at 5% in water | qs pH 5.5 ± 0.3 | qs pH 5.5 ± 0.3 |

Preparation of the Compositions

The starting materials are first weighed out carefully using a balance (precision=0.01 g).

The components of phase A1 are heated to 70° C. using a hotplate, and are mixed using a Rayneri blender.

The polymer of phase A2 is then introduced into phase A1 at 70° C. with stirring using a Rayneri blender, until a homogeneous clear mixture is obtained.

Phase A3 is then introduced into phase A1+A2 at 70° C.

Phase B is heated to 70° C., then introduced into phase A1+A2+A3. The emulsification is carried out at 70° C. using a rotor-stator of Moritz type. After 10 minutes of emulsion, the preparation is brought back to ambient temperature.

Phase C is introduced into the emulsion A1+A2+A3+B, with Rayneri stirring at ambient temperature.

Phase D is introduced into the preparation.

The pH is adjusted at the end of formulation using 5% citric acid in water constituting phase E, to pH=5.5±0.3.

The following results were obtained:

|  |  | 4 | 5 |
|---|---|---|---|
| Visco | | 12.1 P | 5.8 P |
| Stability after 2 months at 45° C. | | YES | YES |
| in vitro SPF | | 10.1 ± 1.2 | 10.2 ± 0.8 |
| Mattness (Score by sensory expert panel, out of 15; 1 = Shiny; 15 = Non-shiny) | | 11.5 ± 1.6 | 11.5 ± 1.6 |
| Tack (Score by sensory expert panel, out of 15; 1 = Very tacky; 15 = Non-tacky) | | 13.5 ± 1.2 | 13.1 ± 2.1 |
| Non-greasy finish (Score by sensory expert panel, out of 15; 1 = Greasy finish; 15 = Non-greasy finish) | | 10.1 ± 1.3 | 11.8 ± 0.3 |
| Colorimetric evaluation of the compositions | L* | 90.8 | 92.2 |
| | a* | −1 | −2.4 |
| | b* | 2.7 | 5.1 |
| | C* | 2.9 | 5.6 |
| | Colour | Pale yellow | Pale yellow |

The compositions are stable and have a pale yellow colour. Applied to the skin, they provide a matt and non-greasy finish.

Examples 7-9: Compositions in O/W Emulsion Form

The following compositions according to the invention were prepared.

| Phases | Composition (% by weight) | 7 invention | 8 invention | 9 invention |
|---|---|---|---|---|
| A1 | WATER | qs 100 | qs 100 | qs 100 |
| A1 | PHENOXYETHANOL | 0.5 | 0.5 | 0.5 |
| A1 | EDTA | 0.1 | 0.1 | 0.1 |
| A1 | GLYCEROL | 5 | 5 | 5 |
| A2 | WATER | 8 | 8 | 8 |
| A2 | SCUTELLARIA BAICALENSIS EXTRACT (BAICALIN 95 MM sold by MMP) | 0.25 | 0.25 | 0.25 |
| A2 | TRIETHANOLAMINE | 0.17 | 0.17 | 0.17 |
| A3 | ACRYLATES COPOLYMER (CARBOPOL AQUA SF1 POLYMER from LUBRIZOL) (30% AM) | | | 0.6 AM |
| A3 | TRIETHANOLAMINE | | | 0.25 |
| A3 | WATER | | | 5 |
| B | Polymer 1 | 2 | 2 | 4 |
| B | DICAPRYLYL CARBONATE (CETIOL CC from COGNIS) | 15 | 15 | 15 |
| B | ISONONYL ISONONANOATE | 2.5 | 2.5 | 2.5 |
| B | DIMETHICONE (Viscosity: 5 cSt) | 3 | 3 | 3 |
| B | GLYCERYL STEARATE (and) PEG-100 STEARATE (ARLACEL 165 from CRODA) | 2 | | |
| B | CETYL ALCOHOL | 1 | | |
| B | POTASSIUM CETYL PHOSPHATE (AMPHISOL K from DSM) | | 2 | |
| B | PARAFFIN WAX (SASOLWAX 5603 from SASOL) | 0.5 | 0.5 | 0.5 |
| B | VITAMIN E | 1 | 1 | 1 |
| C | AMMONIUM ACRYLOYLDIMETHYLTAURATE/ VP COPOLYMER (95% AM) (ARISTOFLEX AVC from CLARIANT) | 1.23 AM | 1.23 AM | 0.475 AM |
| D | TALC | 2 | 2 | 2 |
| E | CITRIC ACID at 5% in water | qs pH 5.5 ± 0.3 | qs pH 5.5 ± 0.3 | qs pH 5.5 ± 0.3 |

Preparation of the Compositions

The starting materials are first weighed out carefully using a balance (precision=0.01 g).

The components of phase A1 are heated to 70° C. using a hotplate, and are mixed using a Rayneri blender.

The polymer of phase A2 is then introduced into phase A1 at 70° C. with stirring using a Rayneri blender, until a homogeneous clear mixture is obtained.

Phase A3 is then introduced into phase A1+A2 at 70° C.

Phase B is heated to 70° C., then introduced into phase A1+A2+A3. The emulsification is carried out at 70° C. using a rotor-stator of Moritz type. After 10 minutes of emulsion, the preparation is brought back to ambient temperature.

Phase C is introduced into the emulsion A1+A2+A3+B, with Rayneri stirring at ambient temperature.

Phase D is introduced into the preparation.

The pH is adjusted at the end of formulation using 5% citric acid in water constituting phase E, to pH=5.5±0.3.

The compositions are stable and have a pale yellow colour. Applied to the skin, they provide a matt and non-greasy finish.

The invention claimed is:

1. A composition comprising:

a) from 0.01% to 10% by weight based upon the total weight of the composition of baicalin and/or at least one derivative thereof or a plant extract comprising baicalin and/or at least one derivative thereof; and b) between 0.1% and 10% by weight based upon the total weight of the composition of one or more polymers comprising monomer units of formulae (A) and (B):

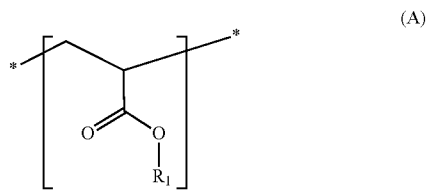

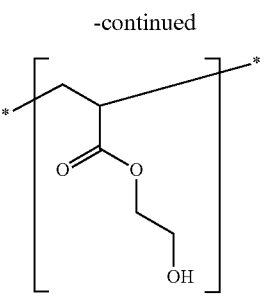

in which:
R₁, independently of one another, is chosen from alkyl or alkylene radicals,
and
at least 60% by weight of the $R_1$ groups are behenyl radicals, the percentage by weight relating to the sum of all the $R_1$ groups present in the polymer,
and
the weight ratio of the sum of all the hydroxyethyl acrylate units to the sum of all the acrylate units bearing the $R_1$ group ranges from 1:30 to 1:1;
and the sum of the total of units A and B is at least 95% by weight of the total weight of the polymer,
the polymer having a number-average molecular weight Mn ranging from 2000 to 9000 g/mol.

2. The composition according to claim 1, in which the baicalin and derivatives thereof are chosen from the compounds of formula (I):

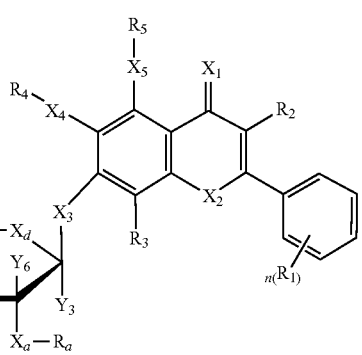

in which:
each $X_1$, $X_2$, $X_3$, $X_4$, $X_5$, $X_a$, $X_b$, $X_c$, $X_d$, $X_e$ and $X_f$ independently denotes O or S;
each $Y_1$, $Y_2$, $Y_3$, $Y_4$, $Y_6$ independently denotes H or a $(C_1-C_{10})$alkyl radical;
each $R_4$, $R_5$, $R_a$, $R_b$ and $R_c$, independently denotes H, a $(C_1-C_{10})$alkyl radical optionally substituted with 1 to 5 groups $R_y$, or a $(C_1-C_{10})$alkyl-O—$(C_1-C_{10})$alkyl radical, each $(C_1-C_{10})$alkyl radical possibly being substituted with 1 to 5 groups $R_y$;
each $R_y$, independently denotes $R_q$ or a —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$tricycloalkenyl, phenyl, naphthyl, —$(C_{14})$aryl radical, each possibly being substituted with one or more radicals $R_z$;
each $R_1$, $R_2$, $R_3$, independently denotes $R_q$ or a —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$tricycloalkenyl, phenyl, naphthyl, —$(C_{14})$aryl radical, each possibly being substituted with one or more radicals $R_z$;
Rf is H, $(C_1-C_{12})$ alkyl optionally substituted with 1 to 5 radicals $R_y$, $(C_1-C_{12})$alkyl-O—$(C_1-C_{12})$alkyl, each $(C_1-C_{12})$alkyl radical possibly being substituted with 1 to 5 groups $R_y$;
each $R_q$, independently is CN, OH, halogen, $N_3$, $NO_2$, $N(R_z)_2$, =$NR_z$, CH=$NR_z$, $NR_z$OH, $OR_z$, $COR_z$, C(O)$R_z$, O(CO)$OR_z$, $SR_z$, S(O)$R_z$ or S(O)$_2R_z$;
each $R_z$, independently is —$(C_1-C_6)$alkyl, —$(C_2-C_6)$alkenyl, —$(C_3-C_8)$cycloalkyl, —$(C_3-C_8)$cycloalkenyl, phenyl, a heterocycle having 3 to 5 branches, CH(halo)₂ or C(halo)₃; and
n is 0, 1, 2, 3, 4 or 5;
and the salts thereof, the optical isomers thereof and the diastereoisomers thereof.

3. The composition according to claim 1, comprising the baicalin corresponding to general formula (II) below:

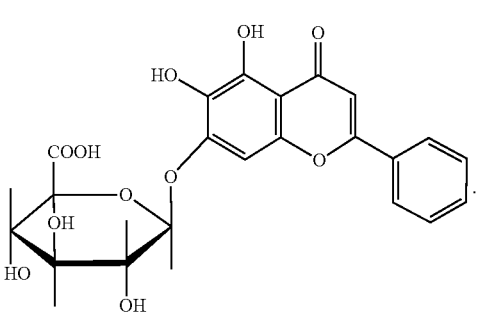

4. The composition according to claim 1, in which the baicalin and/or derivatives thereof are present in active material concentrations ranging from 0.02% to 8% by weight relative to the total weight of the composition.

5. The composition according to claim 1, in which, in the polymer b), $R_1$ is constituted of alkyl radicals.

6. The composition according to claim 1, in which, in the polymer b), at least 70% by weight of the $R_1$ groups are behenyl radicals.

7. The composition according to claim 1, in which, in the polymer b), all the $R_1$ groups are behenyl radicals.

8. The composition according to claim 1, in which, in the polymer b), the weight ratio of the sum of all the hydroxyethyl acrylate units to the sum of all the acrylate units bearing the $R_1$ group ranges from 1:15 to 1:1.

9. The composition according to claim 1, in which the polymer units present in the polymer b) are constituted of the units (A) and (B).

10. The composition according to claim 1, in which the polymer b) has a number-average molecular weight Mn ranging from 5000 to 9000 g/mol.

11. The composition according to claim 1, in which the polymer b) has a melting point ranging from 60° C. to 69° C.

12. The composition according to claim 1, in which the active material concentration of said polymer(s) b) is between 0.5% and 8% by weight relative to the total weight of the composition.

13. The composition according to claim 1, also comprising at least one UV-screening agent.

14. The composition according to claim 1, in the form of an oil-in-water or water-in-oil, emulsion or in the form of a gel.

15. The composition according to claim 1, in which the pH is between 5.1 and 5.9.

16. The composition according to claim 2, in which the baicalin and/or derivatives thereof are present in active material concentrations ranging from 0.01% to 10% by weight relative to the total weight of the composition.

17. The composition according to claim 1, being in the form of an oil-in-water emulsion, having a pH between 5.1 and 5.9, and wherein the baicalin and/or derivatives thereof are present in active material concentrations ranging from 0.02% to 8% by weight, relative to the total weight of the composition; the active material concentration of the polymer(s) b) is between 0.5% and 8% by weight relative to the total weight of the composition, wherein the baicalin and derivatives thereof are chosen from the compounds of formula (I):

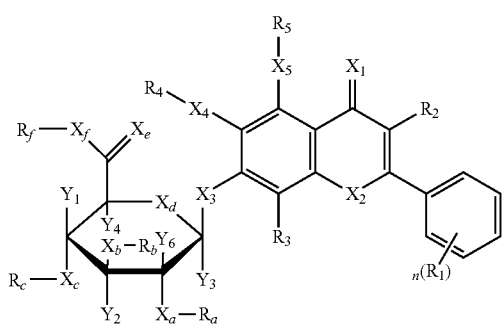

(I)

in which:
each $X_1$, $X_2$, $X_3$, $X_4$, $X_5$, $X_a$, $X_b$, $X_c$, $X_d$, $X_e$ and $X_f$, independently denotes O or S;

each $Y_1$, $Y_2$, $Y_3$, $Y_4$, $Y_6$ independently denotes H or a $(C_1-C_{10})$alkyl radical; each $R_4$, $R_5$, $R_a$, $R_b$ and $R_c$, independently denotes H, a $(C_1-C_{10})$alkyl radical optionally substituted with 1 to 5 groups $R_y$, or a $(C_1-C_{10})$alkyl-O—$(C_1-C_{10})$alkyl radical, each $(C_1-C_{10})$alkyl radical possibly being substituted with 1 to 5 groups $R_y$; each $R_y$, independently denotes $R_q$ or a —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$tricycloalkenyl, phenyl, naphthyl, —$(C_{14})$aryl radical, each possibly being substituted with one or more radicals $R_z$; each $R_1$, $R_2$, $R_3$, independently denotes $R_q$ or a —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$tricycloalkenyl, phenyl, naphthyl, —$(C_{14})$aryl radical, each possibly being substituted with one or more radicals $R_z$;

Rf is H, $(C_1-C_{12})$ alkyl optionally substituted with 1 to 5 radicals $R_y$, $(C_1-C_{12})$alkyl-O—$(C_1-C_{12})$alkyl, each $(C_1-C_{12})$alkyl radical possibly being substituted with 1 to 5 groups $R_y$;

each $R_q$, independently is CN, OH, halogen, $N_3$, $NO_2$, $N(R_z)_2$, =$NR_z$, CH=$NR_z$, $NR_z$OH, $OR_z$, $COR_z$, $C(O)R_z$, $O(CO)OR_z$, $SR_z$, $S(O)R_z$ or $S(O)_2R_z$;

each $R_z$, independently is —$(C_1-C_6)$alkyl, —$(C_2-C_6)$alkenyl, —$(C_3-C_8)$cycloalkyl, —$(C_3-C_8)$cycloalkenyl, phenyl, a heterocycle having 3 to 5 branches, CH(halo)$_2$ or C(halo)$_3$; and n is 0, 1, 2, 3, 4 or 5; and the salts thereof, the optical isomers thereof and the diastereoisomers thereof and the polymer b) has a melting point ranging from 60° C. to 69° C.

* * * * *